(12) United States Patent
McLaughlin et al.

(10) Patent No.: US 11,452,504 B2
(45) Date of Patent: Sep. 27, 2022

(54) REGIONAL CONTRAST ENHANCEMENT BASED ON COMPLEMENTARY INFORMATION TO REFLECTIVITY INFORMATION

(71) Applicant: Shenzhen Mindray Bio-Medical Electronics Co., Ltd., Shenzhen (CN)

(72) Inventors: Glen W. McLaughlin, San Carlos, CA (US); David J. Napolitano, Pleasanton, CA (US)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 167 days.

(21) Appl. No.: 16/792,762

(22) Filed: Feb. 17, 2020

(65) Prior Publication Data

US 2020/0315585 A1    Oct. 8, 2020

Related U.S. Application Data

(60) Provisional application No. 62/827,984, filed on Apr. 2, 2019.

(51) Int. Cl.
*A61B 8/08* (2006.01)

(52) U.S. Cl.
CPC .......... *A61B 8/5207* (2013.01); *A61B 8/5246* (2013.01); *A61B 8/5269* (2013.01)

(58) Field of Classification Search
CPC ............... A61B 8/5207; A61B 8/5269; A61B 8/5246; A61B 8/5292; A61B 8/085; A61B 8/5223; A61B 8/0883; A61B 8/4483; A61B 8/4488
See application file for complete search history.

(56) References Cited

U.S. PATENT DOCUMENTS

| | | | | |
|---|---|---|---|---|
| 5,218,869 A | * | 6/1993 | Pummer | G01S 7/52046 600/442 |
| 2004/0015079 A1 | * | 1/2004 | Berger | A61B 8/56 600/443 |

(Continued)

OTHER PUBLICATIONS

Laing, A. C., and Robinovitch, S. N. (Oct. 9, 2008). "The Force Attenuation Provided by Hip Protectors Depends on Impact Velocity, Pelvic Size, and Soft Tissue Stiffness." ASME. J Biomech Eng. Dec. 2008; 130(6): 061005. https://doi.org/10.1115/1.2979867 (Year: 2008).*

*Primary Examiner* — Joseph M Santos Rodriguez
*Assistant Examiner* — Kaitlyn E Sebastian
(74) *Attorney, Agent, or Firm* — Kory D. Christensen (57) ABSTRACT

Systems and methods for performing ultrasound imaging. Ultrasound information of a subject region in response to ultrasound pulses transmitted toward the subject region can be gathered. The ultrasound information can include reflectivity information and complementary information to the reflectivity information of the subject region in response to the ultrasound pulses. One or more ultrasound images of at least a portion of the subject region can be formed from the reflectivity information. Further, the one or more ultrasound images can be modified based on the complementary information to the reflectivity information to generate one or more enhanced ultrasound images from the one or more ultrasound images.

13 Claims, 8 Drawing Sheets

(56) References Cited

U.S. PATENT DOCUMENTS

| | | | |
|---|---|---|---|
| 2009/0149750 A1* | 6/2009 | Matsumura | A61B 5/0048 600/438 |
| 2012/0108973 A1* | 5/2012 | Osumi | A61B 8/06 600/443 |
| 2013/0218012 A1* | 8/2013 | Specht | G01S 15/8929 600/438 |
| 2014/0276049 A1* | 9/2014 | Doherty | A61B 8/485 600/438 |
| 2016/0038123 A1* | 2/2016 | Duric | A61B 8/5207 600/443 |
| 2017/0340310 A1* | 11/2017 | Carlini | A61B 8/0825 |
| 2018/0008237 A1* | 1/2018 | Venkataraman | A61B 8/12 |
| 2019/0282200 A1* | 9/2019 | Choi | G01S 15/8925 |
| 2021/0219941 A1* | 7/2021 | Tsutaoka | G01S 7/52046 |

* cited by examiner

REGIONAL CONTRAST ENHANCEMENT BASED ON COMPLEMENTARY INFORMATION TO REFLECTIVITY INFORMATION

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)).

Priority Applications:

This application claims priority to U.S. Provisional Patent Application No. 62/827,984 to Glen W. McLaughlin et al., titled SOUND SPEED ESTIMATION FOR THE USE OF REGIONAL CONTRAST ENHANCEMENT OF GRAY SCALE IMAGES, and filed Apr. 2, 2019, the entire disclosure of which is hereby incorporated herein by this reference.

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

TECHNICAL FIELD

The present disclosure relates to ultrasound imaging and more particularly to modifying ultrasound images based on complementary information to reflectivity information.

BACKGROUND OF THE INVENTION

Ultrasound imaging is widely used for examining a wide range of materials and objects across a wide array of different applications. Ultrasound imaging provides a fast and easy tool for analyzing materials and objects in a non-invasive manner. As a result, ultrasound imaging is especially common in the practice of medicine as an ailment diagnosis, treatment, and prevention tool. Specifically, because of its relatively non-invasive nature, low cost and fast response time ultrasound imaging is widely used throughout the medical industry to diagnose and prevent ailments. Further, as ultrasound imaging is based on non-ionizing radiation it does not carry the same risks as other diagnosis imaging tools, such as X-ray imaging or other types of imaging systems that use ionizing radiation.

Ultrasound images typically suffer from limited contrast resolution as a number of clinically significant structures have similar echogenicity to that of background tissue. This limitation has resulted in physicians using other imaging modalities to more easily visualize the contrast resolution between healthy and disease tissue. Several techniques have been developed in order to improve the overall contrast resolution of ultrasound images, e.g. for purposes of improving contrast resolution for background tissue having similar echogenicity. Specifically, techniques for compounding images of either different frequencies, different orientations, or different nonlinear tissue properties have been developed, e.g. harmonic imaging has been developed. While such techniques do provide improvements in contrast resolution in ultrasound images, the amount of contrast resolution capable of being achieved through these techniques is still deficient.

SUMMARY

According to various embodiments, a method for performing ultrasound imaging includes collecting ultrasound information of a subject region in response to ultrasound pulses transmitted toward the subject region. The ultrasound information can include both reflectivity information and complementary information to the reflectivity information of the subject region in response to the ultrasound pulses. The method can also include forming one or more ultrasound images of at least a portion of the subject region from the reflectivity information. Further, the method can include modifying the one or more ultrasound images based on the complementary information to the reflectivity information to generate one or more enhanced ultrasound images from the one or more ultrasound images.

In certain embodiments, a system for performing ultrasound imaging includes an ultrasound transducer and a main processing console. The ultrasound transducer can collect ultrasound information of a subject region in response to ultrasound pulses transmitted toward the subject region. The ultrasound information can include both reflectivity information and complementary information to the reflectivity information of the subject region in response to the ultrasound pulses. The main processing console can form one or more ultrasound images of at least a portion of the subject region from the reflectivity information. The main processing console can also modify the one or more ultrasound images based on the complementary information to the reflectivity information to generate one or more enhanced ultrasound images from the one or more ultrasound images.

In various embodiments, a system for performing ultrasound imaging includes one or more processors and a computer-readable medium providing instructions accessible to the one or more processors to cause the one or more processors to collect ultrasound information of a subject region in response to ultrasound pulses transmitted toward the subject region. The ultrasound information can include both reflectivity information and complementary information to the reflectivity information of the subject region in response to the ultrasound pulses. The instructions can further cause the one or more processors to form one or more ultrasound images of at least a portion of the subject region from the reflectivity information. Additionally, the instructions can cause the one or more processors to modify the one or more ultrasound images based on the complementary information to the reflectivity information to generate one or more enhanced ultrasound images from the one or more ultrasound images.

DETAILED DESCRIPTION

Enhancing ultrasound images continues to be an important area of focus. Specifically, it is critical that ultrasound images can be enhanced to accurately display information related to different types of tissue, e.g. in the same ultrasound image. In turn, this can allow doctors to more easily diagnose diseases and provide treatments for the diseases based on their diagnoses.

In particular, as clinically significant structures often times have similar echogenicity to that of background tissue, it becomes very difficult to create ultrasound images that represent distinguishing characteristics between the structures and the background tissue. For example, ultrasound images typically suffer from limited contrast resolution as a number of clinically significant structures have similar echogenicity to that of background tissue. In turn, it becomes difficult for doctors to quickly and accurately diagnose diseases based on these images and provide treatments for such diseases.

Many attempts have been made to characterize underlying tissue properties with ultrasound. One technology, in particular, has been used to measure the speed of sound propagation within the tissue. However, obtaining a high-resolution sound speed map that can be used to correct for wave dispersion of an ultrasound transmit can be difficult to calculate. This makes it more difficult to characterize underlying tissue properties through ultrasound and ultimately provide the ability for doctors to quickly and accurately provide medical diagnoses and treatment.

The following disclosure describes systems, methods, and computer-readable media for solving these problems/discrepancies. Specifically, the present technology involves system, methods, and computer-readable media for collecting complementary information to reflectivity information generated through ultrasound pulses and enhancing or otherwise modifying ultrasound images based on the complementary information. More specifically, the present technology involves systems, methods, and computer-readable media for identifying one or more regions to modify in an ultrasound image based on complementary information to reflectivity information used to generate the image. In turn, the one or more regions can be modified based on the complementary information, e.g. to enhance the quality of the ultrasound image or the contrast in the ultrasound image.

Specifically and as will be discussed in greater detail later, a low-resolution sound speed map can be generated based on collected complementary information to reflectivity information. In turn, the sound speed map can be applied to enhance the contrast resolution of a B-Mode ultrasound image. The data used to produce the sound speed map and the B-Mode image can be identical and generated through the same transmit/receive profile(s). Alternatively, the data used to produce the sound speed map and the B-mode image can be distinctly gathered through separate transmit/receive profiles, e.g. to optimize the performance of each of the modalities.

Reference is now made to the figures, where like components are designated by like reference numerals throughout the disclosure. Some of the infrastructure that can be used with embodiments disclosed herein is already available, such as general-purpose computers, computer programming tools and techniques, digital storage media, and communications networks. A computing device may include a processor such as a microprocessor, microcontroller, logic circuitry, or the like. The processor may include a special purpose processing device such as an Application-Specific Integrated Circuit (ASIC), Programmable Array Logic (PAL), Programmable Logic Array (PLA), Programmable Logic Device (PLD), Field-Programmable Gate Array (FPGA), or other customized or programmable device. The computing device may also include a computer-readable storage device such as non-volatile memory, static RAM, dynamic Random Access Memory (RAM), Read-Only Memory (ROM), Compact Disc Read-Only Memory (CD-ROM), disk, tape, magnetic, optical, flash memory, or other non-transitory computer-readable storage medium.

Various aspects of certain embodiments may be implemented using hardware, software, firmware, or a combination thereof. As used herein, a software module or component may include any type of computer instruction or computer executable code located within or on a computer-readable storage medium. A software module may, for instance, comprise one or more physical or logical blocks of computer instructions, which may be organized as a routine, program, object, component, data structure, etc., which performs one or more tasks or implements particular abstract data types.

In certain embodiments, a particular software module may comprise disparate instructions stored in different locations of a computer-readable storage medium, which together implement the described functionality of the module. Indeed, a module may comprise a single instruction or many instructions, and may be distributed over several different code segments, among different programs, and across several computer-readable storage media. Some embodiments may be practiced in a distributed computing environment where tasks are performed by a remote processing device linked through a communications network.

The embodiments of the disclosure will be best understood by reference to the drawings. The components of the disclosed embodiments, as generally described and illustrated in the figures herein, could be arranged and designed in a wide variety of different configurations. Furthermore, the features, structures, and operations associated with one embodiment may be applicable to or combined with the features, structures, or operations described in conjunction with another embodiment. In other instances, well-known structures, materials, or operations are not shown or described in detail to avoid obscuring aspects of this disclosure.

Thus, the following detailed description of the embodiments of the systems and methods of the disclosure is not intended to limit the scope of the disclosure, as claimed, but is merely representative of possible embodiments. In addition, the steps of a method do not necessarily need to be executed in any specific order, or even sequentially, nor need the steps be executed only once.

Figure 1:
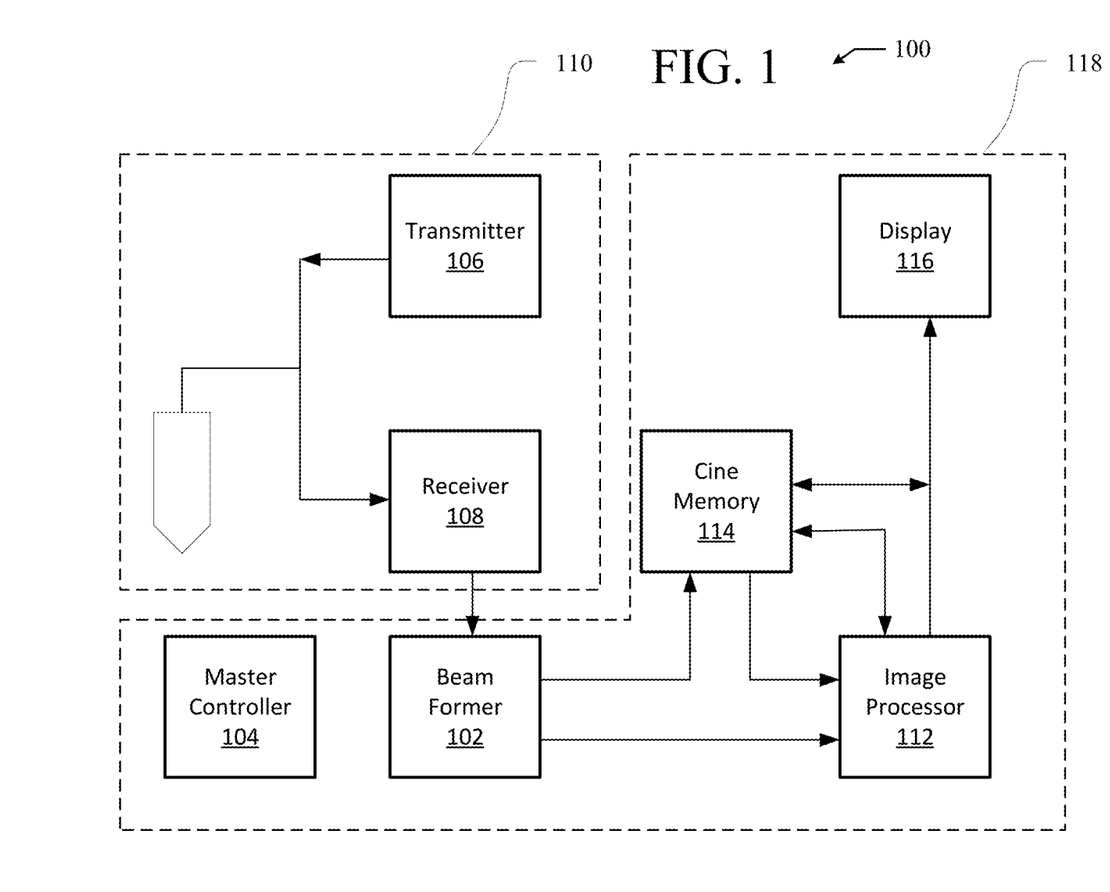
FIG. 1 illustrates an example of an ultrasound system.

FIG. 1 is a schematic block diagram of one exemplary embodiment of a medical imaging device, such as an ultrasound imaging device 100. Those skilled in the art will recognize that the principles disclosed herein may be applied to a variety of medical imaging devices, including, without limitation, an X-ray imaging device, a computed tomography (CT) imaging device, a magnetic resonance imaging (MRI) device, and a positron-emission tomography (PET) imaging device. As such, the components of each device may vary from what is illustrated in FIG. 1.

In one embodiment, the ultrasound imaging device 100 may include an array focusing unit, referred to herein as a beam former 102, by which image formation can be performed on a scanline-by-scanline basis. The device may be controlled by a master controller 104, implemented by a microprocessor or the like, which accepts operator inputs through an operator interface and in turn controls the various subsystems of the device 100.

For each scanline, a transmitter 106 generates a radio-frequency (RF) excitation voltage pulse waveform and applies it with appropriate timing across a transmit aperture (defined, in one embodiment, by a sub-array of active elements) to generate a focused acoustic beam along the scanline.

RF echoes received by one or more receive apertures or receiver 108 are amplified, filtered, and then fed into the beam former 102, which may perform dynamic receive focusing, i.e., realignment of the RF signals that originate from the same locations along various scan lines. Collectively, the transmitter 106 and receiver 108 may be components of a transducer 110. Various types of transducers 110 are known in the ultrasound imaging art, such as linear probes, curvilinear probes, and phased array probes.

An image processor 112 may perform processing tasks specific to various active imaging mode(s) including 2D scan conversion that transforms the image data from an acoustic line grid into an X-Y pixel image for display. For other modes, such as a spectral Doppler mode, the image processor 112 may perform wall filtering followed by spectral analysis of Doppler-shifted signal samples using typically a sliding Fast Fourier Transform (FFT)-window. The image processor 112 may also generate a stereo audio signal output corresponding to forward and reverse flow signals. In cooperation with the master controller 104, the image processor 112 may also format images from two or more active imaging modes, including display annotation, graphics overlays and replay of cine loops and recorded timeline data.

A cine memory 114 provides resident digital image storage to enable single image or multiple image loop review, and acts as a buffer for transfer of images to digital archival devices, such as hard disk drives or optical storage. In some systems, the video images at the end of the data processing path may be stored to the cine memory. In state-of-the-art systems, amplitude-detected, beamformed data may also be stored in cine memory 114. For spectral Doppler mode, wall-filtered, baseband Doppler I/Q data for a user-selected range gate may be stored in cine memory 114. Subsequently, a display 116, such as a computer monitor, may display ultrasound images created by the image processor 112 and/or images using data stored in the cine memory 114.

The beam former 102, the master controller 104, the image processor 112, the cine memory 114, and the display 116 can be included as part of a main processing console 118 of the ultrasound imaging device 100, which may include more or fewer components or subsystems than are illustrated. The ultrasound transducer 110 may be incorporated into an apparatus that is separate from the main processing console 118, e.g. in a separate apparatus that is wired or wirelessly connected to the main processing console 118. This allows for easier manipulation of the ultrasound transducer 110 when performing specific ultrasound procedures on a patient. Further, the transducer 110 can be an array transducer that includes an array of transmitting and receiving elements for transmitting and receiving ultrasound waves.

Those skilled in the art will recognize that a wide variety of ultrasound imaging devices are available on the market, and additional details relating to how images are generated is unnecessary for a thorough understanding of the principles disclosed herein. Specifically, the systems, methods, and computer-readable media described herein can be applied through an applicable ultrasound imaging device of the wide variety of ultrasound imaging devices available on the market.

Figure 2:
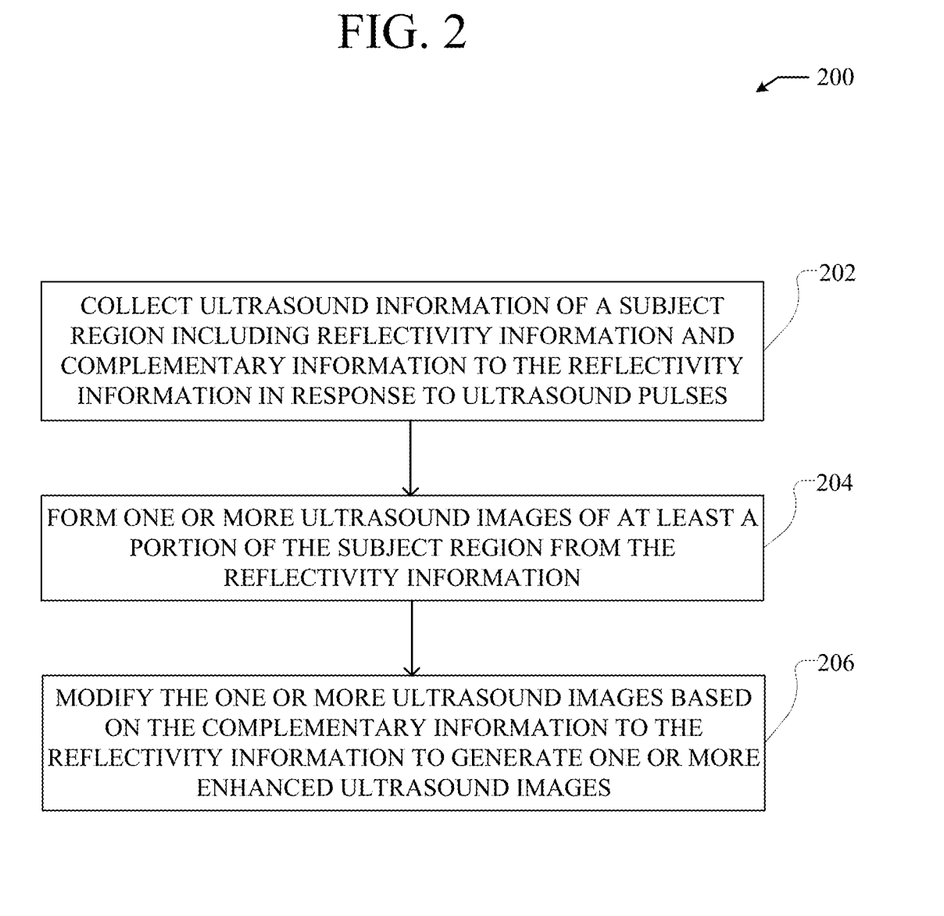
FIG. 2 is a flowchart of an example method for modifying an ultrasound image based on complementary information to reflectivity information of ultrasound pulses used in generating the ultrasound image.

FIG. 2 is a flowchart 200 of an example method for modifying an ultrasound image based on complementary information to reflectivity information of ultrasound pulses used in generating the ultrasound image. The example method shown in FIG. 2, and other methods and techniques for ultrasound imaging described herein, can be performed by an applicable ultrasound imaging system, such as the ultrasound system 100 shown in FIG. 1. For example, the techniques for ultrasound imaging described herein can be implemented using either or both the ultrasound transducer 110 and the main processing console 118, e.g. the image processor 112, of the ultrasound system 100.

At step 202, ultrasound information of a subject region is collected. The ultrasound information includes both reflectivity information and complementary information to the reflectivity information generated in response to ultrasound pulses transmitted towards the subject region. Specifically, reflectivity information generated based on the interaction of ultrasound pulses with the subject region can be collected at step 202. Further, complementary information to the reflectivity information generated based on the interaction of ultrasound pulses with the subject region can be collected at step 202. The reflectivity information and the complementary information can be generated by an applicable ultrasound component, such as ultrasound transducer 110 shown in FIG. 1.

Reflectivity information includes applicable information used in generating ultrasound images of at least a portion of the subject region. Specifically, reflectivity information can include information of reflections of ultrasound pulses transmitted into the subject region, e.g. information of backscattered ultrasound pulses. In turn and as will be discussed in greater detail later, the information of the reflections can be used to generate ultrasound images through an applicable imaging/image formation technique.

Complementary information to the reflectivity information includes applicable information that can be gathered from the ultrasound pulses transmitted towards the subject region. Specifically, complementary information to the reflectivity information can include applicable information that can be gathered form the ultrasound pulses that is not used in directly forming ultrasound images. Specifically, complementary information to the reflectivity information can include propagation speeds of the ultrasound pulses in interacting with the subject region, information related to elasticity of the subject region, information related to stiffness of the subject region, and values of an acoustic non-linearity parameter associated with the subject region. For example, complementary information can include sound speeds of ultrasound pulses as the pulses interact with the subject region and are reflected from the subject region. In another example, complementary information to the reflectivity information can include variations in lateral spatial spectral signals at varying depths.

The reflectivity information and the complementary information can be generated through the same ultrasound pulses transmitted towards the subject region. Specifically, the reflectivity information and the complementary information to the reflectivity information can be generated through the same ultrasound transmit and receive profile(s). For example, a B-Mode image can be produced by compounding across frames, e.g. 2 to 9 frames, of image data. As follows the same ultrasound pulses used in creating the compounded frames of image data can also be used to produce a number, e.g. 2 to 9, of sounds speed maps. In turn, the sound speed maps can be combined to generate an accurate estimate of sound speeds.

Further, the reflectivity information and the complementary information can be distinctly generated through different ultrasound pulses transmitted towards the subject region. Specifically, the reflectivity information and the complementary information can be distinctly generated through separate ultrasound transmit and receive profiles. For example, a first ultrasound transmit and receive profile can be applied to generate the reflectivity information and a second ultrasound transmit and receive profile can be applied to generate the complementary information separately from the reflectivity information. For example and with respect to propagation speed as the complementary information, an ideal transmit profile for estimating propagation speed is not necessarily an optimized profile for B-Mode imaging, and vice versa. Accordingly, the complementary information for identifying the propagation speed can be generated separately from the reflectivity information for performing B-mode imaging.

The reflectivity information and the complementary information can be generated through the same ultrasound transmit receive profile(s) based on characteristics of the subject region. Specifically, the reflectivity information and the complementary information can be created through the ultrasound transmit receive profile(s) if the tissue being imaged is fast moving. For example, if the heart is the subject region, then reflectivity information and the complementary information can be generated through the same ultrasound pulses transmitted towards the heart as the heart is a fast moving structure. Additionally, the reflectivity information and the complementary information can be distinctly generated through different ultrasound transmit receive profiles based on characteristics of the subject region. Specifically, the reflectivity information and the complementary information can be created through different ultrasound transmit receive profiles if the tissue being imaged is slow moving. For example, if the thyroid is the subject region, then the reflectivity information and the complementary information can be generated through different ultrasound pulses transmitted towards the thyroid as the thyroid is a slow moving structure.

The complementary information can be generated over a plurality of ultrasound transmit and receive profiles to generate compound complementary information. For example and as discussed previously, a plurality of sound speed maps can be generated across a plurality of ultrasound transmit and receive profiles to generate compound complementary information including the plurality of sound speed maps. Further in the example, the plurality of sound speed maps can be compounded or otherwise combined to form a compound sound speed map of the compound complementary information. The compound complementary information can be generated through a plurality of transmit and receive profiles that are separate from transmit and receive profile(s) used in creating the reflectivity information. Further, the compound complementary information can be generated through a plurality of transmit and receive profiles that are also used to create the reflectivity information. The compound complementary information, as will be discussed in greater detail later, can be applied to modify the one or more ultrasound images generated from the reflectivity information.

In forming the compound complementary information across a plurality of ultrasound transmit and receive profiles, artifacts can be filtered out from the complementary information used in generating the compound complementary information. Specifically, the complementary information can be combined, when forming the compound complementary information, to filter out artifacts from the complementary information. For example, when multiple sound speed maps are created through different transmit origins, artifacts that are generated in each map will not be collocated across the sound speed maps with respect to the subject region. In turn, when the sound speed maps are combined the total number of artifacts in a combined sound speed map, e.g. the compound complementary information, can be reduced or otherwise eliminated. This can lead to improvements in enhancing or otherwise modifying ultrasound images with the compound complementary information.

At step 204, one or more ultrasound images of at least a portion of the subject region are formed from the reflectivity information. Ultrasound images formed at step 204 can be generated from the reflectivity information using an applicable technique. Specifically, B-Mode ultrasound images can be formed from the reflectivity information through one or more applicable B-Mode imaging techniques. Examples of B-Mode imaging techniques include a fundamental imaging technique, a fundamental spatial compounding imaging technique, a harmonic imaging technique, a harmonic spatial compounding imaging technique, a fundamental and harmonic compounding imaging technique, and a fundamental and harmonic spatial compounding imaging technique.

At step 206, the one or more ultrasound images are modified based on the complementary information to the reflectivity information to generate one or more enhanced ultrasound images. Specifically, the ultrasound images can be modified to present information related to the subject region in a more clear and accurate manner. For example, a contrast in the images can be modified to more clearly show different regions corresponding to different types of tissue in the images of the subject region.

In modifying the one or more ultrasound images based on the complementary information, one or more regions can be identified in the ultrasound images based on the complementary information. In turn, the identified regions in the ultrasound images can be modified or enhanced, e.g. in response to identifying the one or more regions, to ultimately modify the one or more ultrasound images. For example, regions in an ultrasound image corresponding to heart tissue in the subject region can be identified based on the complementary information. As follows, the regions in the ultrasound image corresponding to the heart tissue can be modified or otherwise enhanced to highlight the heart tissue in the ultrasound image.

The one or more ultrasound images can be modified based on a relation of the complementary information to a mean of the complementary information. The mean of the complementary information can correspond to all or a portion of the entire subject region in the one or more ultrasound images. With respect to propagation speed, a propagation speed mean across all or a portion of the subject region can be identified from the propagation speeds included in the complementary information. In turn, one or more regions in the ultrasound images can be identified based on variations of the propagation speeds with respect to the propagation speed mean. Specifically, the one or more regions can be identified based on variations of the propagation speeds corresponding to the one or more regions and the propagation speed mean. For example, if propagation speeds of ultrasound pulses corresponding to a region vary by a specific amount, e.g. a threshold amount, with respect to a propagation speed mean for the subject region, then the region can be identified in the ultrasound image. Further in the example, the region can be separated from surrounding regions in the ultrasound image if the propagation speeds of ultrasound pulses corresponding to the surrounding regions fail to vary by the specific amount, e.g. the threshold amount, with respect to the propagation speed mean for the subject region.

Additionally, the one or more ultrasound images can be modified based on a relation of the complementary information to one or more absolute values of the complementary information. The absolute value of the complementary information can correspond to all or a portion of the entire subject region in the one or more ultrasound images. With respect to propagation speed, absolute value(s) of variations between a propagation speed mean across all or a portion of the subject region can be identified from the propagation speeds included in the complementary information. In turn, one or more regions in the ultrasound images can be identified based on the absolute value(s) of variations between the propagation speeds and the propagation speed mean. Specifically, the one or more regions can be identified based on absolute value(s) of variations between the propagation speeds corresponding to the one or more regions and the propagation speed mean. For example, if an absolute value of the variation between propagation speeds of ultrasound pulses for a region and a propagation speed mean is greater than a specific amount, e.g. threshold amount, then the region can be identified in the ultrasound image. Further in the example, the region can be separated from surrounding regions in the ultrasound image if absolute value(s) of the variation between propagation speeds of ultrasound pulses of the surrounding regions and the propagation speed mean are less than the specific amount, e.g. the threshold amount.

In modifying the one or more identified regions of the ultrasound image(s), the regions can be modified in an applicable way to distinguish the one or more identified regions from the surrounding areas in the ultrasound image(s). Specifically, the one or more identified regions can be colored to distinguish the region(s) from the surrounding areas to the region(s) in the ultrasound image(s). More specifically, the region(s) can be colored in a specific manner based on the complementary information corresponding to the region(s). For example, the region(s) that have corresponding sound propagation speeds that are above a mean propagation speed can be colored as red. Further in the example, the region(s) that have corresponding sound propagation speeds that are below the mean propagation speed can be colored as blue. In another example, the mean sound speed velocity of tissue can be normalized and regions that deviate from the mean can be colored to produce a transparent color overlay that can be added to a B-Mode image. In turn, this can provide direct information to the clinician as to where there are deviations of the tissue properties as estimated from the sound speed variations.

Further, brightness levels in the one or more identified regions can be modified to distinguish the region(s) from the surrounding areas to the region(s) in the ultrasound image(s). More specifically, the brightness levels in the region(s) can be adjusted based on the complementary information corresponding to the region(s). For example, brightness levels in the region(s) that have corresponding sound propagation speeds that are above a mean propagation speed can be increased. Further in the example, brightness levels in the region(s) that have corresponding sound propagation speeds that are below the mean propagation speed can be decreased.

Additionally, one or more gains for the one or more ultrasound images can be modified as part of modifying the one or more ultrasound images. Specifically, gain(s) of the identified region(s) in the ultrasound images can be modified, e.g. in response to identifying the region(s) in the ultrasound images based on the complementary information. The gains corresponding to the identified regions in the ultrasound images can be modified based on the complementary information, e.g. the same complementary information used to identify the regions. Specifically, the gain of the identified regions in the ultrasound images can be modified based on an amount of variation between complementary information corresponding to the regions and an average of at least a portion of the complementary information.

Gains for the ultrasound images can be adjusted based on propagation speeds of ultrasound pulses corresponding to the ultrasound images. Specifically, gains in the identified regions can be adjusted based on propagation speeds of the ultrasound pulses corresponding to the identified regions. More specifically, gains in the identified regions can be adjusted based on variations between the propagation speeds of the ultrasound pulses corresponding to the identified regions and the propagation speed mean. For example, gains in regions of the ultrasound image(s) with propagation speeds that are greater than the propagation speed mean can be increased and gains in regions of the ultrasound image(s) with propagation speeds that are less than the propagation speed mean can be decreased. Alternatively, gains in regions of the ultrasound image(s) with propagation speeds that are less than the propagation speed mean can be increased and gains in regions of the ultrasound image(s) with propagation speeds that are greater than the propagation speed mean can be decreased.

Further, gains for the ultrasound images can be adjusted based on an amount of variation between the complementary information and an average of at least a portion of the complementary information with respect to a threshold. Specifically, gains for the ultrasound images can be adjusted based on an amount of variation between propagation speeds and the propagation speed mean with respect to a threshold. For example, if the amount of variation between propagation speeds of pulses for a region and the mean propagation speed is greater than a threshold amount, then one or more gains for the region can be increased. Further in the example, if the amount of variation between propagation speeds of pulses for a region and the mean propagation speed is less than the threshold amount, then one or more gains for the region can be decreased. Alternatively, if the amount of variation between propagation speeds of pulses for a region and the mean propagation speed is greater than a threshold amount, then one or more gains for the region can be decreased. In turn, if the amount of variation between propagation speeds of pulses for a region and the mean propagation speed is less than the threshold amount, then one or more gains for the region can be increased. A threshold for applying the techniques described here, e.g. a threshold for adjusting gain, can be defined according to an applicable technique and/or by an applicable entity. For example, an operation of an ultrasound system can define a threshold for selectively adjusting gain in one or more ultrasound images based on the complementary information.

The techniques of identifying the one or more regions in the ultrasound image(s) based on the complementary information and modifying the ultrasound image(s) based on the complementary information can be achieved using one or more sound speed maps. A sound speed map can include a mapping of propagation speeds of ultrasound pulses across the subject region. Further, a sound speed map can correspond to the one or more ultrasound images. Specifically, a region in the sound speed map can correspond to a specific region in an ultrasound image such that propagation speeds of ultrasound pulses in the region of the sound speed map are propagation speeds of ultrasound pulses corresponding to the specific region in the ultrasound image. For example, propagation speeds in a region of the sound speed map can indicate propagation speeds of ultrasound pulses interacting with specific heart tissue. In turn, the portion of an ultrasound that includes the heart tissue can correspond to the region of the sound speed map that indicated the propagation speeds of ultrasound pulses interacting with the heart tissue.

One or more sound speed maps can be generated from the complementary information to the reflectivity information. As follows, the one or more regions in the ultrasound image(s) can be identified using the sound speed map(s). For example, a region can be identified from a sound speed map if the propagation speeds for ultrasound pulses of the region, as indicated by the sound speed map, are above a mean propagation speed. In turn, the one or more regions identified using the sound speed map(s) can be modified based on the sound speed map(s).

Figure 3:
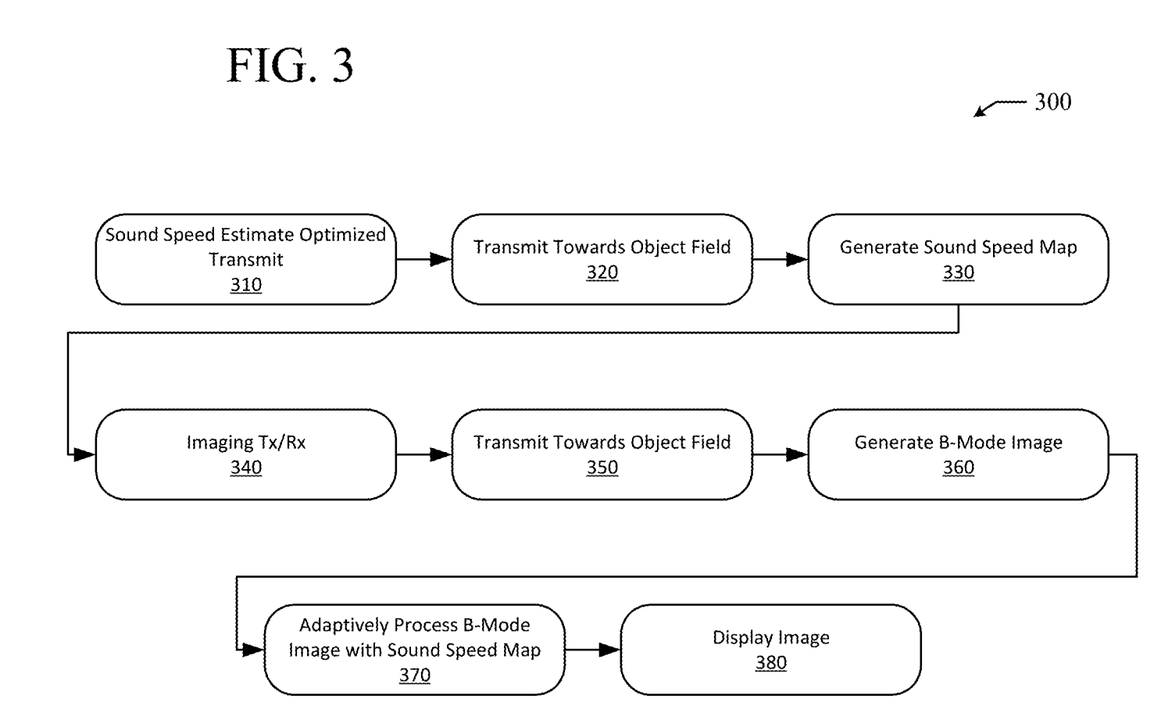
FIG. 3 is a flowchart of an example method for generating an ultrasound image with enhanced contrast resolution through the use of a sound speed map.

FIG. 3 is a flowchart 300 of an example method for generating an ultrasound image with enhanced contrast resolution through the use of a sound speed map. As described previously, the sound speed map can be generated through distinct ultrasound pulses that are separate from the ultrasound pulses used to generate an ultrasound image. Alternatively, the sound speed map can be generated through the same ultrasound pulses that are used to generate an ultrasound image. In the example method shown in the flowchart 300, independent transmit/receive frames are used to generate the sound speed map. Specifically, at step 310 a transmit sequence that is optimized for estimation for the sound speed is identified. At step 320, ultrasound pulses are transmitted towards the object field according to the transmit sequence identified at step 310. Then, at step 330, the backscatter received from the object field is used to generate a sound speed map. At step 340, the imaging Tx/Rx sequence for imaging through B-Mode type imaging is identified. At step 350, ultrasound pulses are transmitted towards the object field according to the imaging Tx/Rx sequence identified at step 340. At step 360, a B-Mode image is generated based on the backscatter from the Tx/Rx sequence. At step 370, the B-Mode image is adaptively processed using the sound speed map. Specifically, regions where the sound speed varies from the normal in the B-Mode Image can be enhanced based on the sound speed map. At step 380, the processed image is displayed.

Figure 4:
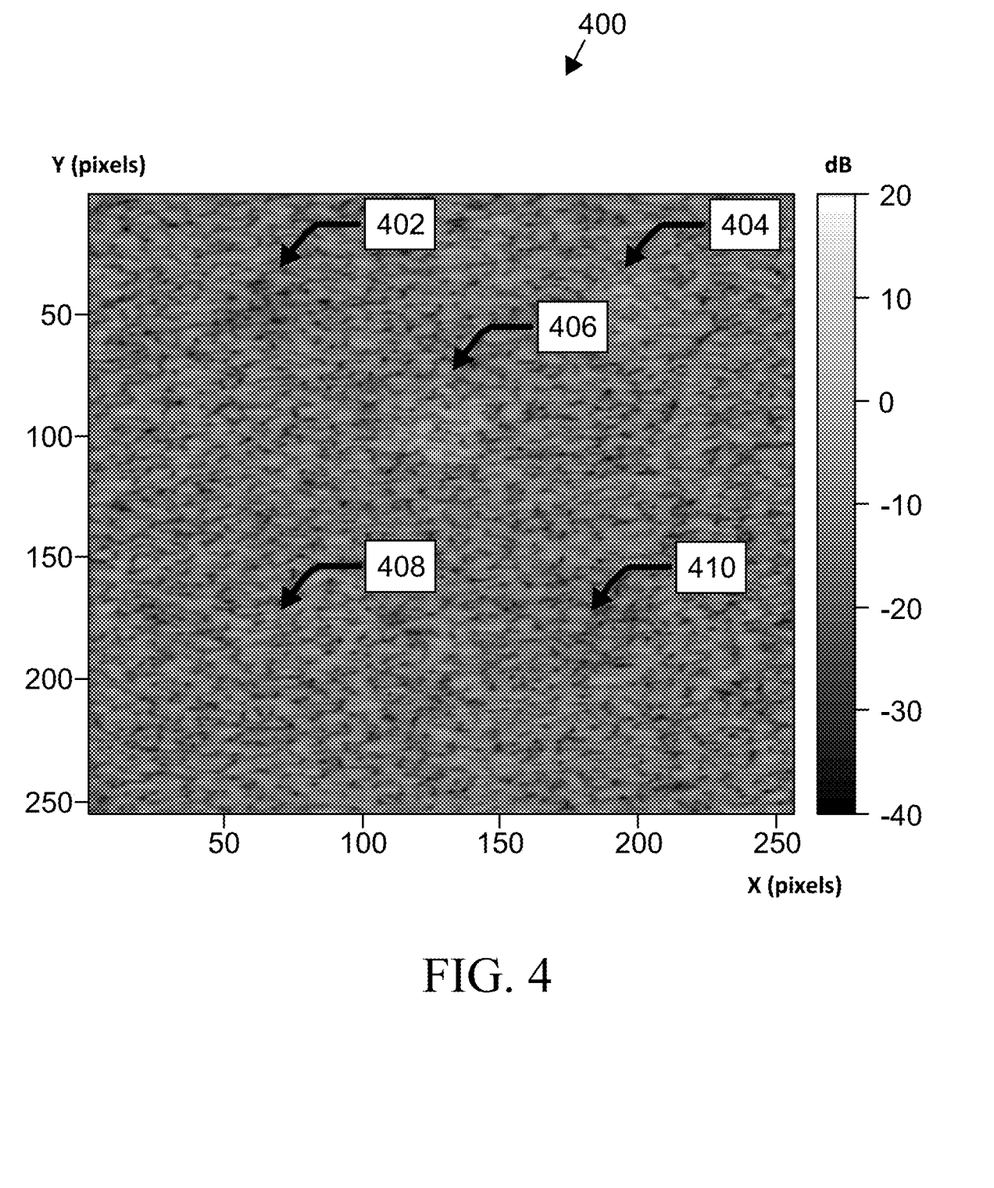
FIG. 4 is an unenhanced B-Mode image with 5 known targets that differ in propagation speed from a mean propagation speed.

FIG. 4 is an unenhanced B-Mode image 400 with 5 known targets that differ in propagation speed from a mean propagation speed. The know targets in the B-Mode image 400 are extremely difficult to see as their backscatter properties only differ slightly from the backscatter properties of the surround regions, e.g. surrounding material. The first target that has a higher sound speed than the mean is located at region 402. The second target that has a lower sound speed than the mean is located at region 404. The third target that has a slightly lower sound speed than the mean is located at region 406. The four target that has a higher sound speed than the mean is located at region 408, and the fifth target that has a lower sound speed than the mean is located at region 410. As shown in the B-mode image 400, it is difficult to accurately visualize where these regions 402-410 are located.

Figure 5:
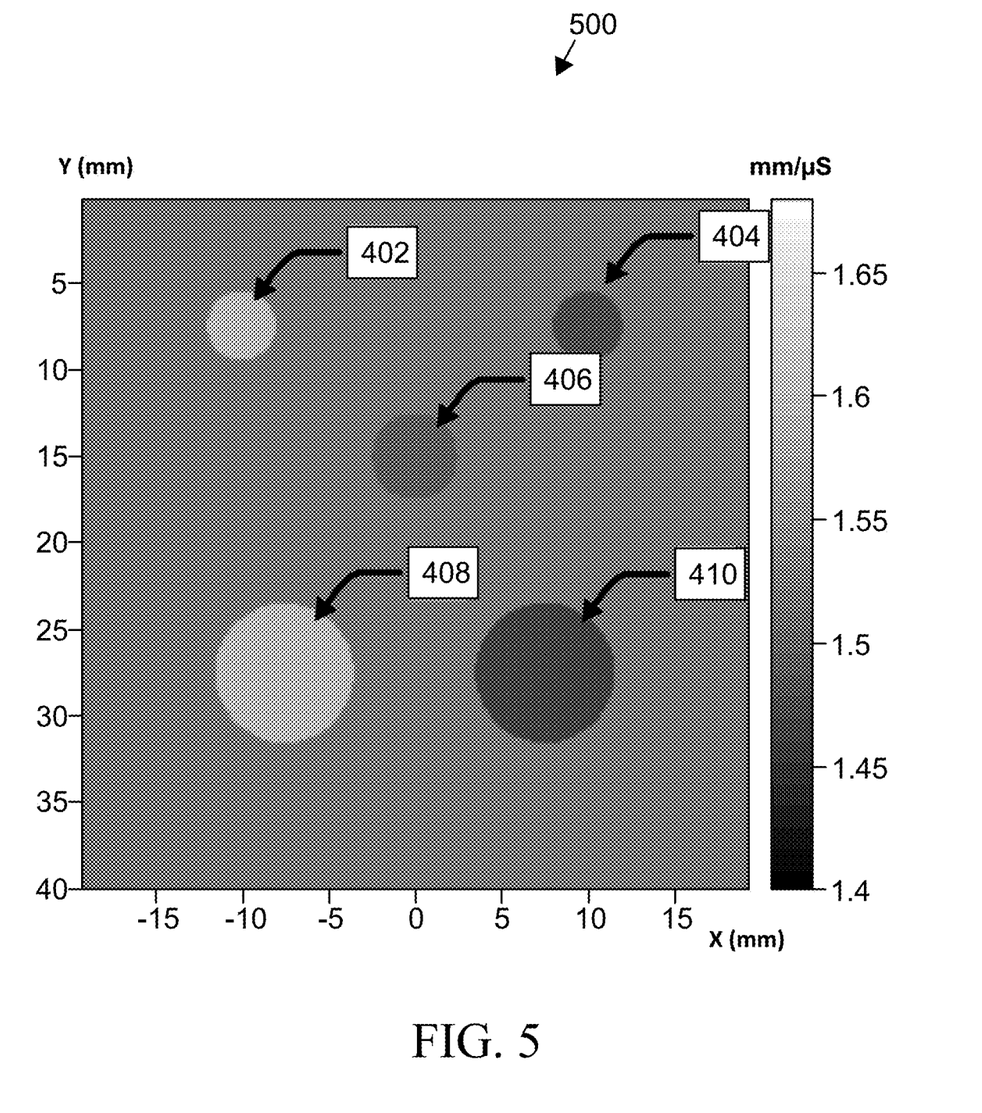
FIG. 5 is a sound speed map of the actual propagation speeds of the ultrasound pulses for the material and the five regions in the B-Mode image shown in FIG. 4.

FIG. 5 is a sound speed map 500 of the actual propagation speeds of the ultrasound pulses for the material and the five regions 402-410 in the B-Mode image 400 shown in FIG. 4. The background sound speed of the phantom, surrounding region to the regions 402-410, is around 1.54 mm/uS. The first region 402 is a small round region that has a corresponding ultrasound propagation speed of around 1.65 mm/uS. The second region 404 is a small round region that has a corresponding ultrasound propagation speed of around 1.45 mm/uS. The third region 406 is a small round region that has a corresponding ultrasound propagation speed of around 1.50 mm/uS. The fourth region 408 is a large round region that has a corresponding ultrasound propagation speed of around 1.65 mm/uS. The fifth region 410 is a large round region that has a corresponding ultrasound propagation speed of around 1.43 mm/uS.

Figure 6:
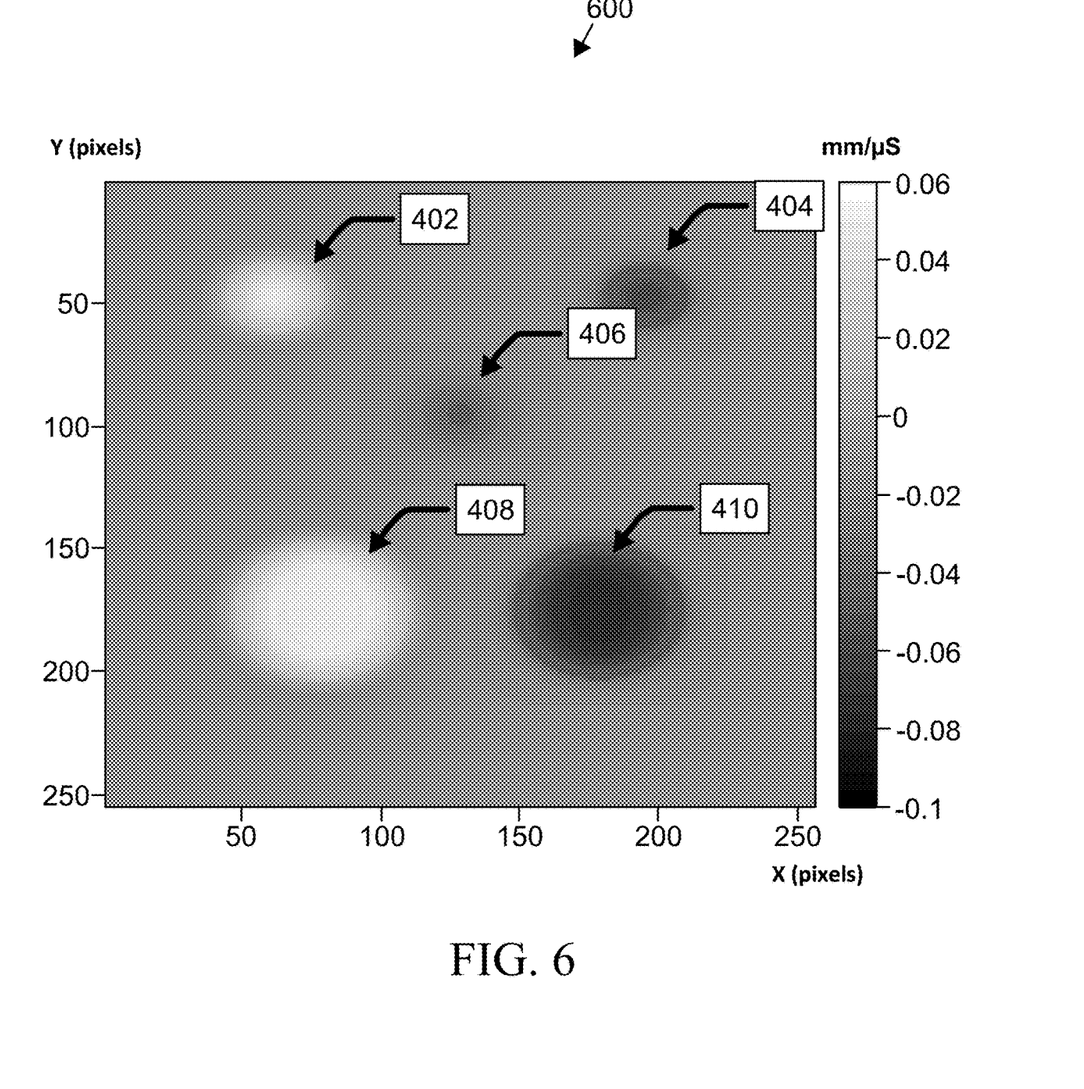
FIG. 6 is a sound speed map of the estimated propagation speed deviations from the mean of the phantom for the material and the five regions for the propagation speeds indicated by the sound speed map shown in FIG. 5.

FIG. 6 is a sound speed map 600 of the estimated propagation speed deviations from the mean of the phantom for the material and the five regions 402-410 for the propagation speeds indicated by the sound speed map 500 shown in FIG. 5. As can be seen the estimates of the sound speed deviations are lower in resolution than the true targets in the phantom as the edges slowly vary back to the mean sound speed instead of have an abrupt change. The first region 402, is estimated to differ by about 0.05 mm/uS from the mean at the center and slowly transition back to the mean propagation speed. The second region 404 is estimated to differ by about −0.06 mm/uS from the mean at the center and slowly transition back to the mean propagation speed. The third region 406 is estimated to differ by about −0.02 mm/uS from the mean at the center and slowly transition back to the mean propagation speed. The fourth region 408 is estimated to differ by about 0.06 mm/uS from the mean at the center and slowly transition back to the mean propagation speed. The fifth region 410 is estimated to differ by about −0.10 mm/uS from the mean at the center and slowly transition back to the mean propagation speed.

The propagation speeds for the sound speed map 500 and the propagation speed deviations shown in the sound speed map 600 can be gathered through a low-resolution method, e.g. using ultrasound pulses operating in a low-resolution imaging or information gathering mode. As shown in FIG. 6, the low-resolution method of obtaining a robust estimate results in the biasing of the propagation speed estimates towards the mean for the smaller region, e.g. 402, 404, and 406. Even though obtaining a robust sound speed map estimate can result in a low-resolution image, this information can still be useful in indicating where there are variations in propagation speed. In turn, the information indicating variation in propagation speed can be used to enhance the contrast resolution of the B-Mode image 400. Further, as more robust higher resolution estimates of propagation speed are capable of being generated, this same adaptive combination of the sound speed map and the B-Mode image only gets better.

Figure 7:
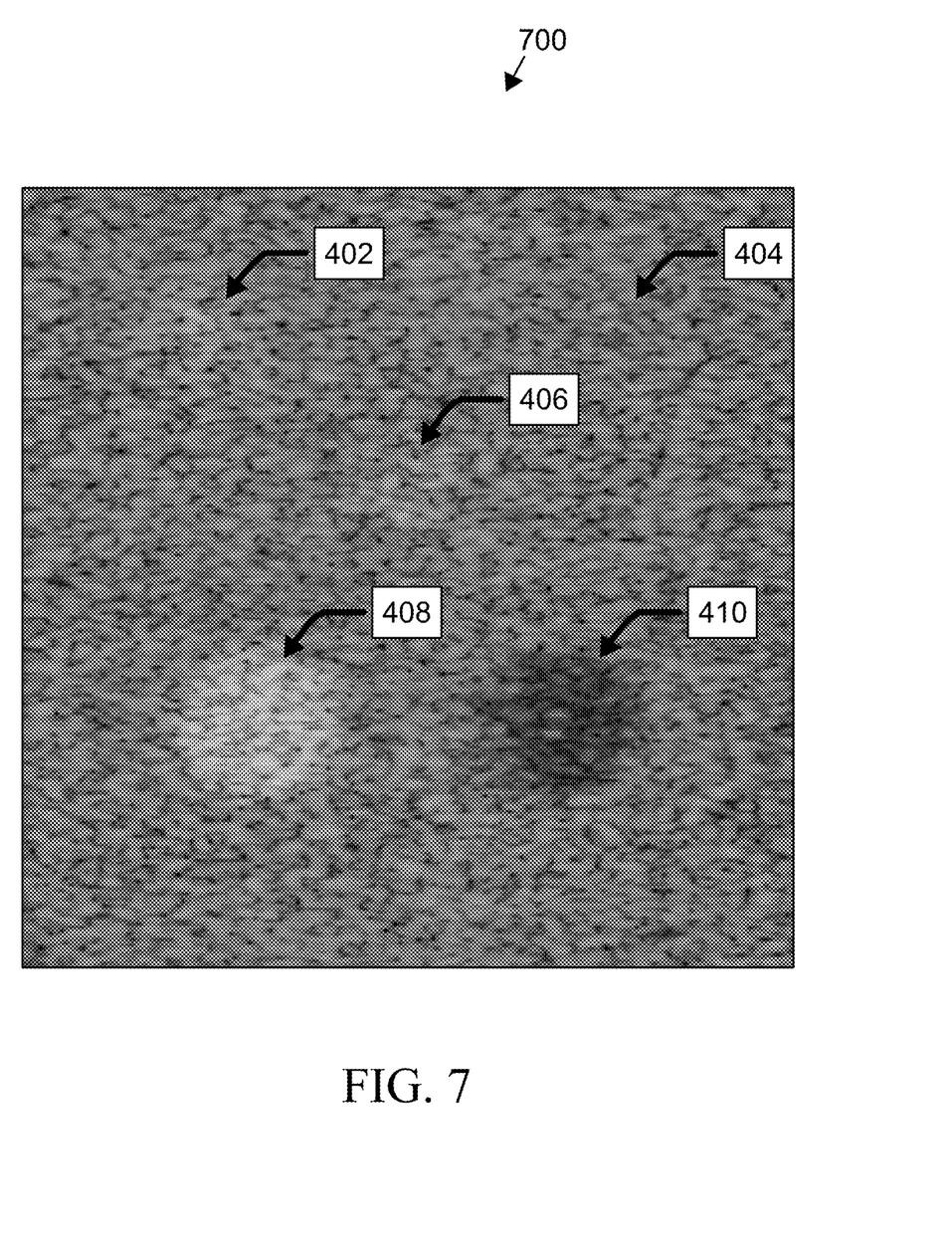
FIG. 7 is a composite image including the B-Mode phantom and the sound speed map overlaid with the mean propagation speed value removed.

FIG. 7 is a composite image 700 including the B-Mode phantom and the sound speed map 600 overlaid with the mean propagation speed value removed. As shown in FIG. 7, the regions are more clearly visible than in the B-Mode image 400 of FIG. 4. The first region 402 shows a small round target where the corresponding ultrasound propagation speed is higher than the background. The second region 404 shows a small round target where the corresponding ultrasound propagation speed is lower than the background. The third region 406 shows a small round target where the corresponding ultrasound propagation speed is lower than the background. The fourth region 408 shows a large round target where the corresponding ultrasound propagation speed is higher than the background. The fifth region 410 shows a large round target where the corresponding ultrasound propagation speed is lower than the background.

Figure 8:
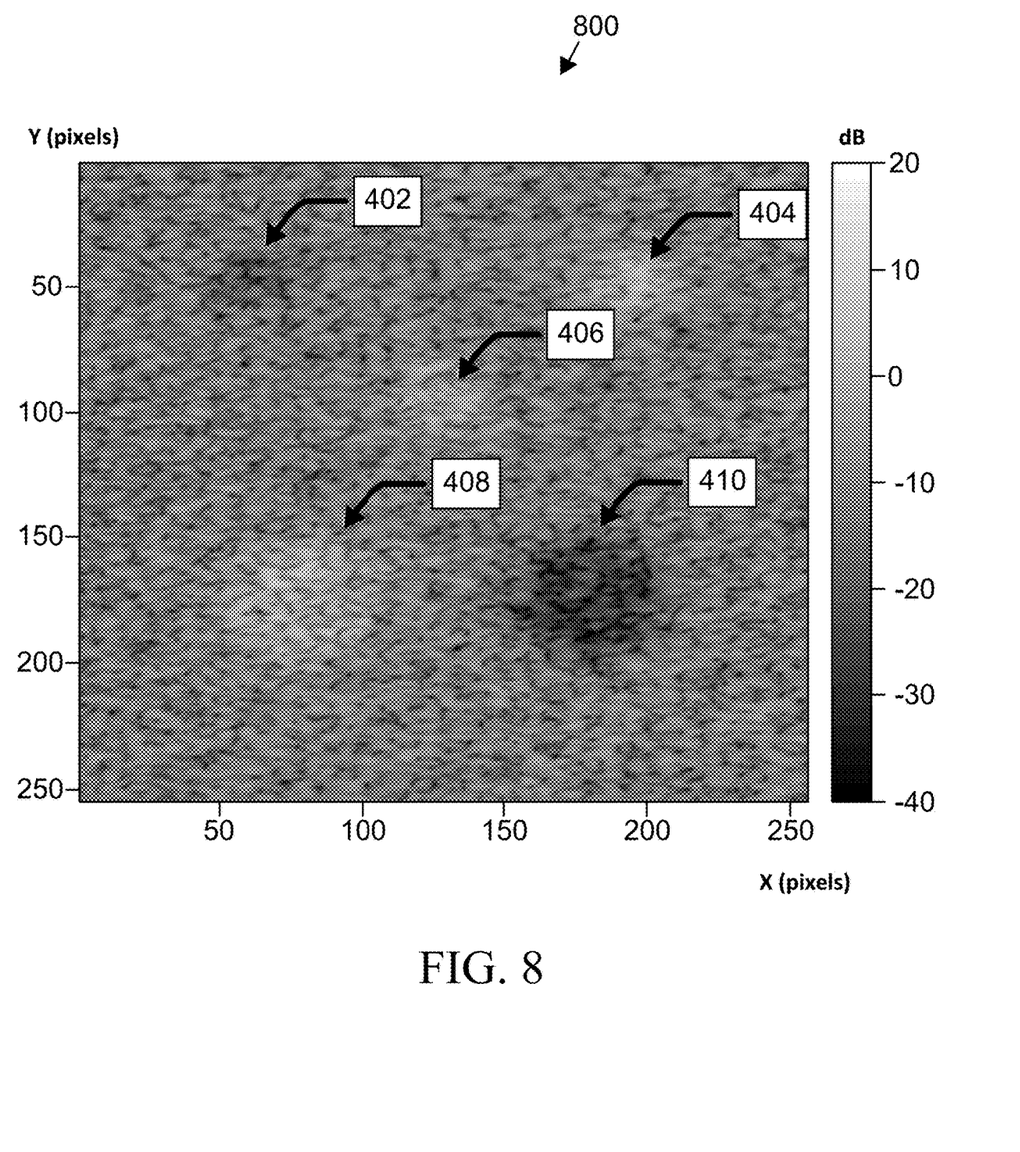
FIG. 8 is an enhanced B-Mode image with contrast resolution that is modified based on the sound speed map to adjust the gain of the areas of differing propagation speeds.

FIG. 8 is an enhanced B-Mode image 800 with contrast resolution that is modified based on the sound speed map 600 to adjust the gain of the areas of differing propagation speeds. Specifically, to create the enhanced B-Mode image 800, the un-altered gray scale level of the subject region is measured from the background of the B-Mode image 400 and enhanced by selectively adjusting the gain in portions of the B-Mode image 400. The degree of gain enhancement that is applied is proportional to each region's 402-410 variation from the mean propagation speed. As can be seen the overall contrast resolution of the regions of varying sound speed are clearly indicated as compared to the B-Mode image 400. The first region 402 has a higher corresponding ultrasound propagation speed than the background and is decreased in gain to clearly show a small round structure. The second region 404 has a lower corresponding ultrasound propagation speed than the background and is increased in gain to clearly show a small round structure. The third region 406 has a lower corresponding ultrasound propagation speed than the background and is increased in gain to clearly show a small round structure. The fourth region 408 has a higher corresponding ultrasound propagation speed than the background and is increased in gain to clearly show a large round structure. The fifth region 410 has a lower corresponding ultrasound propagation speed than the background and is decreased in gain to clearly show a large round structure.

The techniques described herein can be applied in an applicable ultrasound imaging mode, such as B-Mode, contrast-enhanced ultrasound ('CEUS'), CD-Mode, 2D/3D/4D, and the like. Specifically, the techniques described herein are not limited to B-Mode but can also be applied to other modes where improved temporal resolution within a region of interest has substantial clinical benefits, such as CEUS.

This disclosure has been made with reference to various exemplary embodiments including the best mode. However, those skilled in the art will recognize that changes and modifications may be made to the exemplary embodiments without departing from the scope of the present disclosure. For example, various operational steps, as well as components for carrying out operational steps, may be implemented in alternate ways depending upon the particular application or in consideration of any number of cost functions associated with the operation of the system, e.g., one or more of the steps may be deleted, modified, or combined with other steps.

While the principles of this disclosure have been shown in various embodiments, many modifications of structure, arrangements, proportions, elements, materials, and components, which are particularly adapted for a specific environment and operating requirements, may be used without departing from the principles and scope of this disclosure. These and other changes or modifications are intended to be included within the scope of the present disclosure.

The foregoing specification has been described with reference to various embodiments. However, one of ordinary skill in the art will appreciate that various modifications and changes can be made without departing from the scope of the present disclosure. Accordingly, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element. As used herein, the terms "comprises," "comprising," and any other variation thereof, are intended to cover a non-exclusive inclusion, such that a process, a method, an article, or an apparatus that comprises a list of elements does not include only those elements but may include other elements not expressly listed or inherent to such process, method, system, article, or apparatus. Also, as used herein, the terms "coupled," "coupling," and any other variation thereof are intended to cover a physical connection, an electrical connection, a magnetic connection, an optical connection, a communicative connection, a functional connection, and/or any other connection.

Those having skill in the art will appreciate that many changes may be made to the details of the above-described embodiments without departing from the underlying principles of the invention. The scope of the present invention should, therefore, be determined only by the following claims.

What is claimed is:

1. A method for performing ultrasound imaging comprising:
    collecting ultrasound information of a subject region in response to ultrasound pulses transmitted toward the subject region, the ultrasound information including reflectivity information and sound speed information including propagation speeds of the ultrasound pulses interacting with the subject region;
    forming one or more B-mode ultrasound images of at least a portion of the subject region from the reflectivity information;
    calculating, from the sound speed information, a mean propagation speed of the ultrasound pulses interacting with the subject region;
    generating, from the sound speed information, a sound speed map of the propagation speeds of the ultrasound pulses interacting with the subject region; and
    automatically and selectively adjusting gain of different portions of the one or more B-mode ultrasound images in proportion to each portion's variation from the mean propagation speed according to the sound speed map to produce one or more contrast-enhanced B-mode ultrasound images.

2. The method of claim 1, wherein generating the sound speed map comprises generating a plurality of sound speed maps for multiple frames of ultrasound information and compounding the plurality of sound speed maps to produce the sound speed map.

3. The method of claim 1, wherein forming the one or more B-mode ultrasound images comprises using one or more B-mode imaging techniques including one or a combination of a fundamental imaging technique, a fundamental spatial compounding imaging technique, a harmonic imaging technique, a harmonic spatial compounding imaging technique, a fundamental and harmonic compounding imaging technique, and a fundamental and harmonic spatial compounding imaging technique.

4. The method of claim 1, further comprising identifying the portions of the one or more B-mode ultrasound images based on variations between the propagation speeds of the ultrasound pulses in the portions with respect to one or more thresholds.

5. The method of claim 4, further comprising:
identifying a corresponding absolute value of the variations between the propagation speeds and the mean propagation speed for each of the portions of the one or more B-mode ultrasound images; and
modifying the portions of the one or more B-mode ultrasound images based on the corresponding absolute value of the variations between the propagation speeds and the mean propagation speed for each of the portions.

6. The method of claim 1, wherein automatically adjusting further comprises either or both coloring the portions of the one or more B-mode ultrasound images and changing one or more brightness levels in the portions.

7. The method of claim 1, wherein automatically adjusting comprises automatically increasing the gain in the portions where the propagation speeds are higher according to the sound speed map than the mean propagation speed and automatically decreasing the gain in the portions where the propagation speeds according to the sound speed map are less than the mean propagation speed.

8. The method of claim 1, wherein automatically adjusting comprises automatically increasing the gain in the portions where the propagation speeds according to the sound speed map are lower than the mean propagation speed and automatically decreasing the gain in the portions where propagation speeds according to the sound speed map are higher than the mean propagation speed.

9. The method of claim 1, wherein automatically adjusting comprises decreasing the gain in the portions where variations between the propagation speeds according to the sound speed map and the mean propagation speed are higher than a threshold and increasing the gain in the portions where the variations between the propagation speeds according to the sound speed map and the mean propagation speed are lower than the threshold.

10. The method of claim 1, wherein automatically adjusting comprises increasing the gain in the portions where variations between the propagation speeds and the mean propagation speed are higher than a threshold and decreasing the gain in the portions where the variations between the propagation speeds and the mean propagation speed are lower than the threshold.

11. A system for performing ultrasound imaging comprising:
an ultrasound transducer configured to:
collect ultrasound information of a subject region in response to ultrasound pulses transmitted toward the subject region, the ultrasound information including reflectivity information and sound speed information including propagation speeds of the ultrasound pulses interacting with the subject region; and
a main processing console configured to:
form one or more B-mode ultrasound images of at least a portion of the subject region from the reflectivity information;
calculate, from the sound speed information, a mean propagation speed of the ultrasound pulses interacting with the subject region;
generate, from the sound speed information, a sound speed map of the propagation speeds of the ultrasound pulses interacting with the subject region; and
automatically and selectively adjusting gain of different portions of the one or more B-mode ultrasound images in proportion to each portion's variation from the mean propagation speed according to the sound speed map to produce one or more contrast-enhanced B-mode ultrasound images.

12. The method of claim 1, wherein the sound speed map has a lower resolution than the one or more B-mode ultrasound images.

13. The method of claim 1, wherein the reflectivity information and sound speed information are derived from the same ultrasound pulses in response to the subject region including a first amount of motion, and wherein the reflectivity information and sound speed information are derived from different ultrasound pulses in response to the subject region including a second amount of motion, wherein the first amount of motion is greater than the second amount of motion.

* * * * *